United States Patent [19]

Nugent et al.

[11] Patent Number: 4,709,085

[45] Date of Patent: Nov. 24, 1987

[54] CYCLOPROPANATION PROCESS

[75] Inventors: William A. Nugent; Francis J. Waller, both of Wilmington, Del.

[73] Assignee: E. I. Du Pont de Nemours and Company, Wilmington, Del.

[21] Appl. No.: 444

[22] Filed: Jan. 5, 1987

[51] Int. Cl.$^4$ .................. C07C 69/747; C07C 69/743; C07C 69/74
[52] U.S. Cl. .................................. 560/124; 560/102; 560/116; 560/119
[58] Field of Search ................ 560/102, 116, 119, 124

[56] References Cited

U.S. PATENT DOCUMENTS

| | | | |
|---|---|---|---|
| 4,198,527 | 4/1980 | Henrick | 562/506 |
| 4,288,387 | 9/1981 | Crosby | 560/124 |
| 4,474,980 | 10/1984 | Bosone | 560/124 |
| 4,603,218 | 7/1986 | Aratani | 560/102 |

OTHER PUBLICATIONS

Salomon, J.A.C.S., 95, p. 3300, (1973).

Primary Examiner—Michael L. Shippen

[57] ABSTRACT

A process for producing a cyclopropane derivative comprising contacting a diazo compound and an olefinically unsaturated compound in the presence of a catalytic amount of copper cation-exchanged perfluorinated ion exchange polymer is disclosed.

12 Claims, No Drawings

CYCLOPROPANATION PROCESS

FIELD OF THE INVENTION

This invention relates to catalytic processes for producing cyclopropane derivatives.

BACKGROUND OF THE INVENTION

Many transition metals and their complexes have been used as catalysts for the formation of cyclopropanes from olefins and diazo compounds. For many years, copper compounds were favored for their combination of ready availability, low cost and acceptable reactivity with a wide range of olefins and diazo compounds. Recently, homogeneous rhodium cyclopropanation catalysts have been developed which are more active than analogous copper catalysts. Although both heterogeneous and homogeneous copper cyclopropanation catalysts are known, all of the well-known rhodium cyclopropanation catalysts are homogeneous. Improved cyclopropanation catalysts are of considerable interest to the chemical industry.

The earliest reported copper cyclopropanation catalysts were heterogeneous systems. References which are representative of this technology include: Loose, *J. Prakt. Chim.*, 79 (2):505 (1909) which discloses copper bronze; Ebel et al., *Helv. Chim. Acta,* 12:19 (1926) which discloses copper powder; and Skell and Etter, *Chem. Ind.*(London), 6 (1958) which discloses copper sulfate. The following patents disclose heterogeneous copper compounds as cyclopropanation catalysts: U.S. Pat. No. 4,198,527 discloses Cu or $CuSO_4$; U.S.S.R. Patent No. 652,172 discloses CuO; U.S.S.R. Patent No. 576,313 discloses CuO on pumice or alumina; U.S.S.R. Patent No. 4299 discloses $CuSO_4$ on pumice, alumina, activated carbon or Cu chips; Japanese Patent No. 50,116,465 discloses Cu; DE No. 3,244,641 discloses Cu or Cu salts; and European Patent No. 22,608 discloses Cu or Cu salts.

Kirmse, *Carbene Chemistry,* 2nd Ed., (Academic Press, New York, N.Y., 1971) in Chapter 3, reviews both homogeneous and heterogeneous metal catalyzed decompositions of diazo-alkanes, -esters and -ketones. The use of transition metal compounds, including copper and copper salts, as cyclopropanation catalysts is described.

In a more recent review of transition metal catalyzed cyclopropanations, *Catalysis of Organic Reactions,* Ed. by R. L. Augustine,(M. Dekker, New York, N.Y., 1985) in Chapter 4, the author concludes that Rh(II)acetate is generally the most suitable catalyst for intermolecular cyclopropanation reactions. However, Cu(II)triflate (i.e., Cu(II)trifluoromethanesulfonate) in nitromethane is a better catalyst for intramolecular cyclopropanations.

Anciaux et al., *J. Org. Chem.*, 45:695 (1980) disclose a comparison of several rhodium, copper and palladium cyclopropanation catalysts. With few exceptions, the relative efficiencies of three common cyclopropanation catalysts, Rh(II)acetate, Cu(II)triflate and Pd(II)acetate, were found to be Rh>Cu>Pd. The order of selectivity in competitive cyclopropanations is generally Rh<Cu<Pd.

Salomon and Kochi, *J. Amer. Chem. Soc.*, 95:3300 (1973), show that Cu(I), not Cu(II), is probably the active catalyst species in copper-catalyzed cyclopropanations, even when the copper reagent used is nominally Cu(II), e.g. $CuSO_4$, $CuCl_2$, or $Cu(OTf)_2$. This disclosure is consistent with earlier observations reported by others including Komendantov et al., *J. Org. Chem. U.S.S.R.*, 2:561 (1966), and Wittig and Schwarzenbach, *Justus Lieb. Ann. Chem.*, 650:1 (1961).

Campbell and Harper, *J. Chem. Soc.*, 283 (1945), disclose the synthesis of ethyl chrysanthemumates (i.e., 2,2-dimethyl-3-(2-methyl-1-propenyl)-cyclopropanecarboxylic acid ethyl esters) from the copper bronze catalyzed reaction of ethyl diazoacetate with 2,5-dimethyl-2,4-hexadiene. The use of copper catalysts in the synthesis of chrysanthemic acid esters is disclosed in the following references: Japanese Patent No. 49066660, Japanese Patent No. 54073758 and European Patent No. 128012.

Matlin et al., *J. Chem. Soc., Chem. Commun.,* 1038 (1984), disclose a method of attaching a chiral ligand to silica, coordinating Cu(II) or Ni(II) to the immobilized chiral ligand and using this modified silica as a cyclopropanation catalyst. When the substrate olefin is styrene, the catalyst tends to become coated with polystyrene, reducing the activity of the catalyst substantially and limiting the recycle value of the catalyst. Waller, *Catal. Rev. Sci. Eng.,* 28(1):1 (1986), reviews catalysis with metal cation-exchanged resins. U.S. Pat. No. 4,446,329 discloses the preparation of several metal salts of perfluorosulfonic acid polymers, including a Cu(II) salt obtained from the reaction of $Cu(NO_3)_2.xH_2O$ with the acid form of a perfluorosulfonic acid polymer. This (perfluorosulfonic acid polymer)-supported copper salt was shown to be only a slightly active catalyst for the ethylation of benzene, perhaps due to resin fusion at the reaction temperature, 240° C.

Pittman, *Polymer-supported Reactions in Organic Synthesis,* Ed. by P. Hodge and D. C. Sherrington, (Wiley and Sons, 1980) in Chapter 5, reviews catalysis by polymer-supported transition metal complexes. The problem of metal loss due to leaching or chemical changes is disclosed.

SUMMARY OF THE INVENTION

The present invention provides a process for producing a cyclopropane derivative comprising contacting a diazo compound and an olefinically unsaturated compound in the presence of a catalytic amount of copper cation-exchanged perfluorinated ion exchange polymer.

DETAILED DESCRIPTION OF THE INVENTION

The invention resides in a process for catalyzing the reaction of a diazo compound with an olefinically unsaturated compound to form one or more cyclopropane derivatives, wherein the catalyst comprises copper cation-exchanged perfluorinated ion exchange polymer (PFIEP). As used herein, the expression "cyclopropane derivative" refers to a compound containing a substituted three-membered carbocyclic ring. Suitable substituents are compatible with the cyclopropanation process of the present invention. A partial list of suitable substituents includes saturated and unsaturated hydrocarbons, optionally containing heteroatoms, such as, halogens, nitrogen, oxygen, sulphur, or phosphorus. The advantages of using copper cation-exchanged perfluorinated ion exchange polymers as catalysts in this invention include increased catalytic activity over most known cyclopropanation catalysts for a wide range of unsaturated substrates, increased thermal stability of the catalyst due to the high degree of fluorination of the polymer backbone, ease of catalyst preparation and separation from the reaction mixture, and decreased leaching of the catalytic metal from the support compared to analogous rhodium catalysts.

A wide variety of olefinically unsaturated compounds can be employed in the process of the present invention, including compounds with more than one ethylenic group and substituted compounds. It has been found that substituents with Hammett sigma-values less than 0.2, e.g., alkyl, aryl, alkoxy and aryloxy, do not interfere with the cyclopropanation reaction. The Hammett sigma-value is a numerical constant for a specified substituent. This value represents the effect of a selected substituent on the ionization of benzoic acid under standard conditions (water at 25° C.). Sigma-values provide a measure of the electron-withdrawing ($\sigma > 0$) or electron-releasing ($\sigma < 0$) properties of a substituent relative to hydrogen ($\sigma = 0$). A list of representative sigma-values for a variety of common substituents can be found in "Fundamentals of Organic Chemistry", page 571, by C. D. Gutsche and D. J. Pasto, published by Prentice-Hall, 1975. Some electron-withdrawing substituents with Hammett sigma-values greater than 0.2 can also be suitable, but only if the olefin contains no more than two such electron-withdrawing groups. Such substituents include, e.g., halo, acyl, aroyl, and alkoxycarbonyl. The ethylenic unit can be an isolated double bond, or part of a conjugated system.

Acyclic and cyclic double bonds can be cyclopropanated by the present process. A partial list of olefinically unsaturated compounds which can be cyclopropanated by the process include , e.g., propene, butenes, pentenes, hexenes, octenes, decenes, tetradecenes, octadecenes, dococenes, cyclopentene, cyclohexene, cycloheptene, cyclooctene, butadiene, pentadienes, hexadienes, cyclohexadiene, cyclooctadiene, isoprene, styrene, norbornene, vinyl acetate, indene, dihydropyran, 1,1-dichloro-4-methyl-3-pentadiene, 2,5-dimethyl-2,4-hexadiene and norbornadiene. Preferred olefinically unsaturated compounds contain from about 3 to about 20 carbon atoms, and most preferably from about 4 to about 10 carbon atoms. Most preferred olefinically unsaturated compound are selected from the group consisting of 2,5-dimethyl-2,4-hexadiene, styrene, cyclohexene, and 1,1-dichloro-4-methyl-1,3-pentadiene.

Preferred diazo compounds which can be employed in the process of the present invention contain at least one electron-withdrawing substituent which is compatible with the diazo functionality and also has a Hammett sigma-value greater than zero. Most preferred diazo compounds are selected from the group consisting of diazo esters and diazo diesters, e.g., ethyl diazoacetate and diethyl diazodiacetate.

The present process is conducted in the presence of a catalytic amount of a copper cation-exchanged perfluorinated ion exchange polymer. Preferably, the perfluorinated ion-exchange polymer PFIEP is a perfluorinated sulfonic acid polymer (PFIEP[$SO_3H$]) or a blend of perfluorinated sulfonic acid and perfluorinated carboxylic acid polymers (PFIEP[$SO_3H$]/PFIEP[$CO_2H$]). Most preferred perfluorinated sulfonic acid polymers have a number average molecular weight of at least about 5000. Preferably, the PFIEP contains a sufficient number of sulfonic acid groups to give an equivalent weight of from about 500 to about 20,000, and most preferably from about 900 to about 2000. Although the polymer backbone comprises, for the most part, fluorinated carbon atoms, it is not necessary that all other atoms be excluded. For example, ether oxygen atoms may be present in the backbone, as well as in the side chains of the polymer. Such other atoms and or groups as hydrogen (H), chlorine (Cl) and carboxy (COOH) may be present in limited amounts without significantly affecting the stability or operability of the polymer under the process conditions. It is preferred that the polymer contain no greater than about 5 weight percent total of hydrogen and chlorine groups. Representative of suitable perfluorinated ion exchange polymers are the Nafion ® perfluorinated ion exchange polymers, commercially available from E. I. du Pont de Nemours and Company.

Perfluorosulfonic acid polymers may be employed in in a variety of known forms including beads, powders and films. The preparation of blends of perfluorinated sulfonic acid and perfluorinated carboxylic acid polymers is disclosed in U.S. Pat. No. 4,176,215, the disclosure of which is incorporated herein by reference. Preferred blends of perfluorinated sulfonic acid and perfluorinated carboxylic acid polymers include blends of tetrafluoroethylene copolymers with methylperfluoro-5-methyl-4,7-dioxanon-8-eneoate and tetrafluoroethylene copolymers with perfluoro(3,6-dioxa-4-methyl-7-octene) sulfonic acid. Most preferred blends have an ion exchange capacity of at least 0.7 meq/g. Preferably, the ratio of sulfonic acid to carboxylic acid groups in the blend is from about 1:1 to about 10:1, and most preferably from about 2:1 to about 10:1.

Although perfluorinated ion exchange polymers are generally available in the acid (or hydrogen ion) form, it may be desirable to exchange a portion of the acidic hydrogens of the polymer with alkali metal cations, e.g. $K^+$, prior to the formation of the copper cation-exchanged perfluorinated ion exchange polymer. Methods for exchanging cations on perfluorinated ion exchange polymer are well known in the art. Two preferred methods for exchanging $H^+$ by $K^+$ are described in Examples 1 and 5.

Copper salts useful for cation-exchanging into perfluorinated ion exchange polymer to form the catalyst system of the present invention include, but are not limited to, $CuCl_2$, $Cu(NO_3)_2$, $CuSO_4$, $CuCO_3Cu(OH)_2$, $Cu(OTf)_2$, $Cu(OAc)_2$, $CuBr_2$ and $Cu(ClO_4)_2$ and the hydrated salts thereof. Typically, copper is incorporated into perfluorinated ion exchange polymer in the cupric, i.e. Cu(II), form. Although not wishing to be bound by theory, there is evidence that the catalytically reactive form of the metal is Cu(I). It is believed that the diazo compound acts as a reducing agent to convert Cu(II) to Cu(I). Typically, between about 50% and about 98% of the cations or acidic hydrogen atoms of the polymeric support are replaced with copper to form the catalyst system of the present invention. Preferably, between about 50% and about 90% of the cation(s) or acidic hydrogen is replaced with copper. It is believed that maximum cyclopropanation activity is obtained from catalysts with the minimum number of acidic hydrogens.

Preferably, the present process is conducted with a molar ratio of olefinically unsaturated compound to copper of from about 100:1 to about 5000:1, and most preferably from about 400:1 to about 2000:1. Larger ratios may provide too little catalyst to achieve rate enhancement, and smaller ratios are uneconomical with regard to the perfluorinated ion exchange polymer. In addition, the ratio of olefinically unsaturated compound to diazo compound is, preferably, from about 5:1 to about 500:1, and most preferably from about 10:1 to about 100:1. Smaller ratios tend to result in the formation of diazines and diesters due to diazo coupling reactions, and larger ratios are uneconomical with regard to the olefin.

Although a solvent is not required in the present process, it may be advantageous to employ one, particularly when higher molecular weight olefinically unsaturated compounds are used as substrates. Suitable solvents include aromatic hydrocarbons such as benzene or toluene, and chlorinated hydrocarbons such as methylene chloride, and fluorochlorinated solvents such as 1,1,2-trichlorotrifluoroethane.

In a preferred embodiment, the process of the invention is effected by adding a solution of the diazo compound, the olefinically unsaturated compound and an optional solvent slowly, dropwise to a stirred suspension of the catalyst and olefinic substrate. It is desirable to maintain an excess of olefinic substrate relative to diazo compound to minimize the formation of diazines, diesters and other diazo coupling products. In some cases, it may be necessary to heat the reaction mixture during the addition of the diazo compound or after the addition is complete.

Suitable reaction temperatures will depend on the reactivity of the olefin, the stability of the diazo compound and the volatility of the reactants. Preferred reaction temperatures are from about 0° to about 120° C., and most preferably from about 20° to about 80° C. It is not necessary to conduct the process in an inert atmosphere. The reaction time is not critical. The process can be run for periods as long as about 48 hours, but typically the reaction time is from about 0.25 hours to about 24 hours.

As the reaction proceeds, $N_2$ is evolved and the cessation of gas formation can be used to indicate completion of the reaction. When the reaction is complete, the reaction mixture can be filtered to remove the catalyst and the products isolated by standard techniques such as distillation or chromatography.

The catalyst may be reused in further cyclopropanation reactions. The cyclopropanation process of this invention is useful in the preparation of functionalized cyclopropanes, some of which are key intermediates in the manufacture of synthetic pyrethroid insecticides.

The invention is further defined in the following examples wherein all parts, percentages, and equivalents are by weight, mesh sizes are U.S. Standard Sieve units, and all degrees are Celsius unless otherwise noted. Comparative examples are also included to point out the particular advantages of this invention. In the Examples and Comparative Experiments, gas chromatographic analysis was performed on either a ⅛" (3 mm) diameter, 10' (3.05 m) column packed with SE-30ABS. or a 50' (15.3 m) cross-linked methyl silicone fused silica capillary column programmed from 60° to 200° at 8° min$^{-1}$.

EXAMPLE 1

Synthesis of Ethyl Chrysanthemumate Using Cu,K-PFIEP[SO$_3$H]

Catalyst Preparation

A slurry of powder PFIEP[SO$_3$H](200–325 mesh) in the acid form (3.0 g, 2.73 mequiv) was stirred with an aqueous (100 mL) exchanging solution of KCl (1.0 g, 13.4 mmol) for approximately 2 hours at 60°–70°. The exchanging solution was decanted and a fresh exchanging solution was slurried with the partially exchanged powder PFIEP for approximately 4 hours. The resulting K-exchanged resin was filtered, washed with 50 mL distilled water, and dried in a vacuum oven under a stream of $N_2$ at approximately 110° for 2 hours. The resulting dried K-exchanged resin weighed 2.75 g.

The K-exchanged resin was stirred with an aqueous (100 mL) solution of Cu(NO$_3$)$_2$.2H$_2$O (0.6 g, 2.68 mmol) at 60°–70° for 5 hours. The resulting resin was filtered, washed with 50 mL of water, and dried in a vacuum oven under a stream of $N_2$ at about 110° for 3 hours. The resulting dried resin catalyst (Cu,K-PFIEP[SO$_3$H]) weighed 2.5 g. Elemental analysis gave 2.18% Cu and 0.60% K.

Synthesis of Ethyl Chrysanthemumate

A flask was charged with CH$_2$Cl$_2$ (25 mL), 2,5-dimethyl-2,4-hexadiene (25 mL) and 0.45 g of the Cu,K-PFIEP[SO$_3$H] catalyst, prepared as described above. A solution of ethyl diazoacetate (2.5 g) in CH$_2$Cl$_2$ (25 mL) was added slowly dropwise and the resulting reaction mixture was stirred for 24 hours at ambient temperature. Gas chromatography analysis showed that the resulting product contained cis- and trans-ethyl chrysanthemumates in a 1:1.66 isomer ratio and a combined yield of 89.6%.

Comparison Experiment A

Synthesis of Ethyl Chrysanthemumate using Copper Bronze

The reaction described in Example 1 was substantially repeated except that a copper bronze catalyst (90% Cu, 10% Sn), available commercially from B.D.H. Chemicals Ltd., Poole, England (Product #27814), was used in place of the Cu,K-PFIEP[SO$_3$H] catalyst. To induce the reaction, it was necessary to eliminate the CH$_2$Cl$_2$ and heat the reaction mixture to 100°. Only traces of ethyl chrysanthemumate could be detected by gas chromatography analysis.

EXAMPLE 2

Synthesis of Ethyl Chrysanthemumate Using Cu,K-PFIEP[SO$_3$H]

Catalyst Preparation

A slurry of powder PFIEP[SO$_3$H] in the potassium form (11.0 g, 1100 equiv) was stirred with an aqueous (100 mL) exchange solution of Cu(NO$_3$).2H$_2$O (2.4 g, 10.7 mmol) at about 70° for 8.5 hours. The resulting resin was filtered, washed with 100 mL of water and dried in a vacuum oven under a stream of $N_2$ at 110° for 4 h. The dried resin catalyst (Cu,K-PFIEP[SO$_3$H]) weighed 10.8 g. Elemental analysis gave 1.98% Cu, 0.8% K and 0.018% N.

Synthesis of Ethyl Chrysanthemumate

Ethyl diazoacetate (5.0 g) in methylene chloride (50 mL) was added dropwise to a slurry of the Cu,K-PFIEP[SO$_3$H] catalyst described above (2.0 g) in methylene chloride (100 mL) and 2,5-dimethyl-2,4-hexadiene (8.33 g). After stirring for about 18 h at ambient temperature, the reaction product was isolated by filtering off the catalyst, evaporating the solvent and chromatographing the resulting residue on silica with 10% ethyl acetate and 90% hexane as eluant. The isolated chrysanthemumate had an identical $^1$H nmr spectrum to a commercial sample. Anal. Calcd. for $C_{12}H_{20}O_2$: C, 73.43; H, 10.27; Found: C, 74.08; H, 10.58.

EXAMPLES 3 and 4

Synthesis of Ethyl 2-Phenylcyclopropanecarboxylate Using Cu,K-PFIEP[SO$_3$H]

Synthesis of Ethyl 2-Phenylcyclopropanecarboxylate

In Example 3, a flask was charged with 0.5 g of the catalyst described in Example 1, CH$_2$Cl$_2$ (2.5 mL) and styrene (2.5 mL). A solution of ethyl diazoacetate (0.23 g), styrene (10 mL), and CH$_2$Cl$_2$ (10 mL) was added slowly dropwise and the resulting mixture was stirred for 24 hours. Gas chromatographic analysis of the reaction product showed that cis- and trans-ethyl-2-phenyl-cyclopropanecarboxylates had been produced in a combined yield of 91%.

In Example 4, a flask was charged with 1.0 g of the catalyst described in Example 1, CH$_2$Cl$_2$ (2.5 mL), and styrene (2.5 mL). A solution of ethyl diazoacetate (0.23 g), CH$_2$Cl$_2$ (12.5 mL), and styrene (12.5 mL) was added slowly dropwise and the resulting mixture was stirred for 24 hours. The reaction product was analyzed by gas chromatography and the catalyst recovered by filtration. This process was repeated for a total of ten cycles during which yields of ethyl 2-phenylcyclopropane-carboxylate remained essentially constant at about 91%. The recovered catalyst was dried in vacuo. Duplicate elemental analyses gave copper contents of the recovered catalyst of 1.83 and 1.88%.

Comparison Experiment B

Synthesis of Ethyl 2-Phenylcyclopropanecarboxylate using Rh-PFIEP[SO$_3$H] Catalysts Catalyst Preparation A sample of Rh$^{+2}$-exchanged PFIEP was prepared by refluxing a slurry of powder PFIEP[SO$_3$H] (100–400 mesh, 1.4 g, 1.27 mequiv) and Rh$_2$(OAc)$_4$ (0.14 g, 0.317 mmol) in CH$_2$Cl$_2$ (30 mL) for 1.5 hours. The resulting slurry was cooled to ambient temperature and filtered. The resulting resin was washed with CH$_2$Cl$_2$ (10 mL) and air dried to give 1.65 g of light green Rh-PFIEP[SO$_3$H]. Elemental analysis: 3.99% Rh. This represents 0.639 mmol Rh, suggesting that all of the sulfonic acid sites were exchanged.

Synthesis of Ethyl 2-Phenylcyclopropanecarboxylate

A solution of CH$_2$Cl$_2$ (12.5 mL), styrene (12 5 mL) and ethyl diazoacetate (0.25 g, 2.19 mmol) was added slowly dropwise at ambient temperature to a stirred slurry of Rh-PFIEP[SO$_3$H] (1.0 g, 0.387 mmol, prepared as described above), styrene (2.5 mL) and CH$_2$Cl$_2$ (2.5 mL). Gas evolution ceased about 1 hour after the addition of the ethyl diazoacetate solution was complete. The resulting slurry was stirred for 24 hours and then allowed to settle. The solution was removed, the resulting resin was washed with 3.0 mL of CH$_2$Cl$_2$. The solution and the wash were combined and analyzed for cyclopropane products. Yield (based on ethyl diazoacetate): 73.9%.

This procedure was substantially repeated using the washed resin for a total of nine cycles during which yields of ethyl 2-phenylcyclopropanecarboxylate decreased to 32.5%. The color of the exchanged resin changed from green to orange during the third cycle. The color of the decanted solution changed from light green to light yellow on the fourth cycle. The color changes and decreases in yield are presumed to be due to metal leaching.

Comparison Experiment C

Synthesis of Ethyl 2-Phenylcyclopropanecarboxylate Using Cu-Amberlyst ®

Catalyst Preparation

A commercial sample of a polystyrenesulfonic acid resin, commercially available from Rohm & Haas under the registered trademark Amberlyst ® 15 , (5.0 g, 23.5 mequiv) in the acid form was heated to approximately 60° for 2 hours with an exchanging solution of Cu(NO$_3$)$_2$.3H$_2$O (9.9 mmol) dissolved in 100 mL distilled water. The resulting mixture was not stirred in order to prevent breakage of the beads. The exchanging solution was decanted and the procedure was repeated with another 9.9 mmol of Cu(NO$_3$)$_2$.3H$_2$O in 100 mL distilled water. The resulting resin was filtered, washed with distilled water and dried in a vacuum oven under a stream of N$_2$ at about 110° for 3 hours. The dried resin catalyst weighed 4.68 g. Elemental analysis of the Cu-Amberlys ® catalyst gave 12.07% Cu.

Synthesis of Ethyl 2-Phenylcyclopropanecarboxylate

The reaction described in Example 3 was substantially repeated, except that 0.5 g of the Cu-Amberlyst ® catalyst described above was substituted for the Cu,K-PFIEP[SO$_3$H] catalyst. Gas chromatography analysis showed that the yield of ethyl 2-phenylcyclopropanecarboxylates was 60%.

Comparison Experiment D

Synthesis of Ethyl 2-Phenylcyclopropanecarboxylate Using Cu(II)-Triflate

The reaction of Example 3 was substantially repeated except that a 0.05 g of a Cu(II)-triflate catalyst, commercially available from Alfa Products, (Cat.#17245), was employed as a homogeneous catalyst in place of the Cu,K-PFIEP[SO$_3$H] catalyst. The yield of ethyl 2-phenylcyclopropanecarboxylate was 84%. The resulting solution was homogeneous, precluding catalyst recovery by filtration.

EXAMPLE 5

Synthesis of Ethyl 2-Phenylcyclopropanecarboxylate Using Cu,K-PFIEP[SO$_3$H]/PFIEP[CO$_2$H]

Catalyst Preparation

A Cu,K-PFIEP[SO$_3$H]/PFIEP[CO$_2$H] catalyst was prepared by stirring a slurry of powder PFIEP[SO$_3$H]/PFIEP[CO$_2$H] (35–60 mesh, 15 g) in the acid form with aqueous KOH (21.4 mmol) at 80° C. for 4 h. The resulting K-exchanged resin was filtered and washed with distilled water. This resin was stirred with Cu(NO$_3$)$_2$.3H$_2$O (13.6 mmol) at 80° for 4 hours, washed with distilled water and dried in a vacuum oven under a stream of nitrogen at approximately 110° for 2 hours. The dried Cu,K-exchanged resin catalyst weighed 14 g. Elemental analysis: 1.33% K; 1.92% Cu; 8 ppm N.

Synthesis of Ethyl 2-Phenylcyclopropanecarboxylate

The reaction described in Example 3 was substantially repeated except that the Cu,K-PFIEP[SO$_3$H] catalyst was replaced by the Cu,K-PFIEP[SO$_3$H]/PFIEP[CO$_2$H] (0.58 g) catalyst described above. The reaction mixture was allowed to stir for 0.5 hour after the addition of the solution of ethyl diazoacetate, CH$_2$Cl$_2$ and styrene. Analysis by gas chromatography showed that the combined yield of cis- and trans-ethyl-2-phenylcyclopropanecarboxylates was 95%.

EXAMPLES 6-8

Synthesis of Ethyl 7-Norcaranecarboxylate Using Cu,K-PFIEP[SO$_3$H]

In Example 6, a flask was charged with cyclohexene (5 mL) and 1.0 g of the catalyst described in Example 1. A solution of ethyl diazoacetate (0.23 g) in cyclohexene (25 mL) was added slowly dropwise at 25° and the resulting mixture was stirred for 2 hours at ambient temperature. The resulting reaction mixture was analyzed by gas chromatography and was shown to contain cis- and trans-ethyl-7-norcaranecarboxylate in a combined yield of 36%.

In Example 7, the reaction described in Example 6 was substantially repeated except that half of the cyclohexene was replaced by CH$_2$Cl$_2$. A flask was charged with the catalyst described in Example 1, cyclohexene (2.5 mL) and CH$_2$Cl$_2$ (2.5 mL). A solution of ethyl diazoacetate (0.23 g) in cyclohexene (12.5 mL) and CH$_2$Cl$_2$ (12.5 mL) was added slowly dropwise at 25°. After stirring for 24 hours, the yield of ethyl 7-norcaranecarboxylate was 58%.

In Example 8, the reaction described in Example 7 was substantially repeated except that the CH$_2$Cl$_2$ was replaced with 1,1,2-trichlorotrifluoroethane. After stirring for 24 hours, the yield of ethyl 7-norcaranecarboxylate was 36%.

EXAMPLE 9

Synthesis of Ethyl 3-(2,2-Dichlorovinyl)-2,2-Dimethyl-1-Cyclopropanecarboxylate Using Cu,K-PFIEP[SO$_3$H]

A flask was charged with the catalyst described in Example 1 (0.5 g) and 1,1-dichloro-4-methyl-1,3-pentadiene (5 mL) and the resulting suspension heated to 75°. A solution of ethyl diazoacetate (0.23 g) in the diene (20 mL) was added slowly dropwise while the temperature of the catalyst containing solution was maintained at 75°. After stirring for 0.5 hour, the combined yield of cis- and trans-ethyl-3-(2,2-dichlorovinyl)-2,2-dimethyl-1-cyclopropanecarboxylate was determined to be 17% by gas chromatography using a commercial sample as a calibration standard.

EXAMPLE 10

Synthesis of Ethyl 3-(2,2-Dichlorovinyl)-2,2-Dimethyl-1-Cyclopropanecarboxylate Using Cu,K-PFIEP[SO$_3$H]

Catalyst Preparation

A slurry of powder PFIEP[SO$_3$H] in the potassium form (11.0 g, 1100 equiv) was stirred with an aqueous (100 mL) solution of CuCl$_2$. 2H$_2$O (1.7 g, 9.94 mmol) at about 70° C. for 6.75 hours. The resulting resin was filtered, washed with 100 mL of water and dried in a vacuum oven under a stream of N$_2$ at 110° for 4 hours. The dried resin catalyst weighed 10.6 g. Elemental analysis gave 1.75% Cu and 1.26% K.

Synthesis of Ethyl-3-(2,2-Dichlorovinyl)-2,2-Dimethyl-1-Cyclopropanecarboxylate

The reaction described in Example 9 was substantially repeated except that the catalyst was prepared as described above using CuCl$_2$.2H$_2$O as the Cu salt component. The yield of the cyclopropanated product was 12%.

EXAMPLE 11

Synthesis of Ethyl 3-(2,2-Dichlorovinyl)-2,2-Dimethyl-1-Cyclopropanecarboxylate Using Cu,K-PFIEP[SO$_3$H]

Catalyst Preparation

A slurry of powder PFIEP[SO$_3$H] in the potassium form (11.0 g, 1100 equiv. wt.) was stirred with an aqueous (100 mL) solution of Cu(OAc)$_2$. H$_2$O (5.0 mmol) at about 70° for 4.25 hours. The resulting resin was filtered, washed with 100 mL of water and dried in a vacuum oven under a stream of N$_2$ at 110° C. for 4 h. The dried resin catalyst weighed 10.6 g. Elemental analysis gave 1.52% Cu and 1.72% K.

Synthesis of Ethyl-3-(2,2-Dichlorovinyl)-2,2-Dimethyl-1-Cyclopropanecarboxylate

The reaction described in Example 9 was substantially repeated except that the catalyst was prepared as described above using copper(II)acetate as the Cu salt component. The yield of cyclopropanated product was 13%.

What is claimed is:

1. A process for producing a cyclopropane derivative comprising contacting a diazo compound and an olefinically unsaturated compound in the presence of a catalytic amount of copper cation-exchanged perfluorinated ion exchange polymer.

2. A process as defined in claim 1, wherein the perfluorinated ion-exchange polymer is a perfluorinated sulfonic acid polymer or a blend of perfluorinated sulfonic acid and perfluorinated carboxylic acid polymers.

3. A process as defined in claim 2, wherein the perfluorinated ion-exchange polymer is a perfluorinated sulfonic acid polymer having a number average molecular weight of at least about 5000.

4. A process as defined in claim 2, wherein the perfluorinated ion-exchange polymer contains a sufficient number of sulfonic acid groups to give an equivalent weight of from about 500 to about 20,000.

5. A process as defined in claim 4, wherein the perfluorinated ion-exchange polymer contains a sufficient number of sulfonic acid groups to give an equivalent weight of from about 900 to about 2000.

6. A process as defined in claim 1, wherein the olefinically unsaturated compound contains from about 3 to about 20 carbon atoms.

7. A process as defined in claim 6, wherein the olefinically unsaturated compound contains from about 4 to about 10 carbon atoms.

8. A process as defined in claim 7, wherein the olefinically unsaturated compound is selected from the group consisting of 2,5-dimethyl-2,4-hexadiene, styrene, cyclohexene, and 1,1-dichloro-4-methyl-1,3-pentadiene.

9. A process as defined in claim 6, wherein the diazo compound is selected from the group consisting of diazo esters and diazo diesters.

10. A process as defined in claim 9, wherein the diazo compound is ethyl diazoacetate.

11. A process as defined in claim 1, wherein the molar ratio of olefinically unsaturated compound to copper is from about 100:1 to about 5000:1

12. A process as defined in claim 11, wherein the molar ratio of olefinically unsaturated compound to copper is from about 400:1 to about 2000:1.

* * * * *